Figure 1:
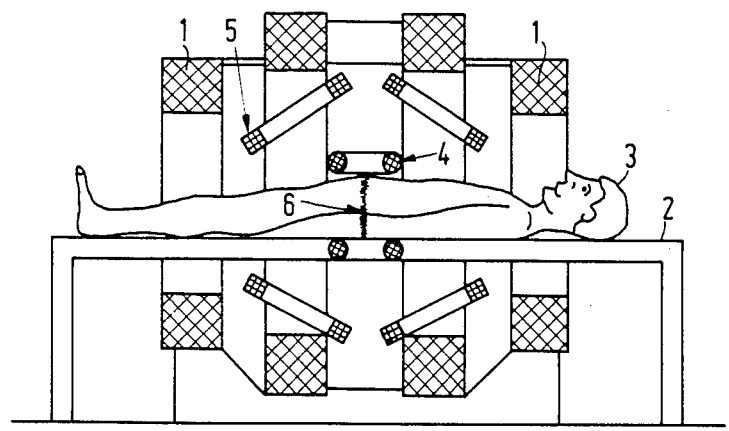

United States Patent [19]

Buikman et al.

[11] Patent Number: 4,694,836
[45] Date of Patent: Sep. 22, 1987

[54] MRI TOMOGRAPHY APPARATUS FOR GENERATING A MOTION SIGNAL

[75] Inventors: Dirk Buikman; Thomas Helzel; Peter Röschman, all of Hamburg, Fed. Rep. of Germany

[73] Assignee: U.S. Philips Corporation, New York, N.Y.

[21] Appl. No.: 809,635

[22] Filed: Dec. 16, 1985

[30] Foreign Application Priority Data

Dec. 21, 1984 [DE]  Fed. Rep. of Germany ....... 3446717
Mar. 21, 1985 [DE]  Fed. Rep. of Germany ....... 3510195

[51] Int. Cl.⁴ ............................................. A61B 5/05
[52] U.S. Cl. .................................. 128/653; 128/721; 324/309; 324/322
[58] Field of Search .................. 128/653, 1.3–1.5, 128/721–723, 716; 324/309, 318, 322

[56] References Cited

U.S. PATENT DOCUMENTS

| | | | |
|---|---|---|---|
| 3,324,848 | 6/1967 | Domeier et al. | 128/722 |
| 3,452,743 | 7/1969 | Rieke | 128/723 |
| 4,315,503 | 2/1982 | Ryaby et al. | 128/419 F |
| 4,387,722 | 6/1983 | Kearns | 128/716 |
| 4,433,693 | 2/1984 | Hochstein | 128/721 |
| 4,474,185 | 10/1984 | Diamond | 128/722 |
| 4,494,553 | 1/1985 | Sciarra et al. | 128/721 |
| 4,545,384 | 10/1985 | Kawachi | 128/722 |
| 4,556,051 | 12/1985 | Maurer | 128/419 F |
| 4,567,893 | 2/1986 | Charles et al. | 128/653 |

OTHER PUBLICATIONS

Schultz et al., "The Effect of Motion on Two-Dimensional Fourier Transformation Magnetic Resonance Images," Radiology, vol. 152, pp. 117–120, Feb. 1984.
Runge et al., "Respiratory Gating in Magnetic Resonance Imaging at 0.5 Tesla," Radiology, May 1984, vol. 151, pp. 521–523.
Schmidt et al., "Physiological Monitoring During NMR Measurements of Animals," Journal of Magnetic Resonance, vol. 54, 1983, pp. 480–485.

Primary Examiner—Lee S. Cohen
Assistant Examiner—Ruth S. Smith
Attorney, Agent, or Firm—Paul R. Miller

[57] ABSTRACT

A method of generating a motion signal which is dependent on motion of a body to be examined in an MRI tomography apparatus, characterized in that during the examination the impedance of a high-frequency coil system (33; 34) whose field acts on the body (3) to be examined and which is tuned to a predetermined resonance frequency is measured in the resonance frequency range with the motion signal being derived from the measurement signal just formed.

14 Claims, 7 Drawing Figures

MRI TOMOGRAPHY APPARATUS FOR GENERATING A MOTION SIGNAL

The invention relates to a method of generating a motion signal which is dependent on motion of a body to be examined in a MRI tomography apparatus. The invention also relates to an MRI tomography apparatus for performing such a method which includes a first high-frequency coil system serving to generate a high-frequency magnetic field having the Larmor frequency and for receiving spin resonance signals.

A MRI tomography apparatus of this kind is known. Generally, the same high frequency coil system is used to generate a high-frequency magnetic field and to receive the spin resonance signal. The term "high-frequency coil system" is to be broadly interpreted. It is to be understood to also include resonators, for example as described in German Patent Application No. P 33 47 597. Thus, a high-frequency magnetic field is generated whose frequency lies in the so-called Larmor frequency range. The Larmor frequency is proportional to the intensity of the static magnetic field generated in the MRI tomography apparatus and amounts to approximately 42.5 MHz/T for hydrogen. The high-frequency magnetic field causes excitation of the spin nuclei in a body to be examined, so that after this field has disappeared the spin resonance signal is induced as a quasi-echo in the high-frequency coil system; and this signal can be further processed by a computer in order to determine the spin nuclei distribution and/or the relaxation times T1, T2 in the body to be examined.

The examination of a body by means of such an MRI tomography apparatus involves a multitude of cycles in which during each cycle the high-frequency magnetic field is generated and the resonance signals are received. Before a high-frequency magnetic field is generated again after reception of a resonance signal, a comparatively long period of time elapses (with an order of magnitude of several 100 ms) so that the overall examination period is comparatively long: generally one minute or more. It will be apparent that motions of the patient being examined, notably respiratory and deglutitory motions, are unavoidable during such long periods of time. These motions are liable to falsify the examination results. In order to avoid this phenomenon, known MRI tomograpy apparatus include a motion detector which detects motions of the patient. Such a motion detector can operate thermally, pneumatically, mechanically, electrically or optically and must be attached to the patient; and the motion signal thus generated must be transmitted via a separate channel. The motion signal thus generated can be used for a substantial reduction of the motional artifacts caused by patients motions.

One possibility in this respect consists in that each of the cycles is started only when the motion signal indicates that the patient body again occupies a defined position (so called triggering). Another possibility consists in that the cycles are completed regardless of the motion signals from the motion detector, preferably at constant intervals, and to omit those spin resonance signals from the reconstruction which have occured during a motion of the body (so-called gating). The cycles which have been disregarded must then be repeated in an identical manner. A combination of both methods, that is to say gating and triggering, is also possible.

It is an object of the present invention to provide an MRI tomography apparatus which allows for simple detection of motions.

In order to achieve this, a method of the kind set forth is extended in that during examination the impedance of a high-frequency coil system whose field acts on the body to be examined and which is tuned to a predetermined resonance frequency is measured in the resonance frequency range with the motion signal being derived from the measurement signal thus formed.

The invention utilizes the fact that the quality factor and the stray capacitance of the high-frequency coil system change in reaction to all motions of the patient situated within the field of the high-frequency coil system, such as, for example, during respiratory, deglutitory, cardiac and peristaltic motions. Thus, the impedance of this coil system also changes with regard to amount and phase. This impedance is measured at least at intervals during the examination in accordance with the invention, and the motion signal can be derived from the measurement signal thus generated, for example by rectification with each value of the impedance being associated with a given motional phase.

Two possibilities exist for performing this method. The first possibility is based on a MRI tomography apparatus which includes an impedance measuring unit for measuring the impedance of the high-frequency coil system used to generate the high-frequency magnetic field and to receive spin resonance signals; and this version is characterized in that the impedance measuring unit is activated during the examination of the body with the measurement signal thus generated being used as the motion signal.

It is to be noted that it is necessary to measure the impedance of the high-frequency coil system of MRI tomography apparatus. This is because the introduction of the patient into the field of the high-frequency coil system influences the quality factor or adaptation and the resonance frequency thereof; therefore, there is provided the impedance measuring unit which acts on adjusting members for the automatic adaption or readjustment of the high-frequency coil system. After the beginning of the actual examination, the impedance measuring unit is no longer activated; and it can then be used for generating the motion signal.

A second possibility consists in that the MRI tomograpy apparatus includes a second high-frequency coil system for generating the motion signal with the impedance of this second coil system being measured by an impedance measuring unit.

The first solution is the simpler one because only one high-frequency coil system is required which then has a dual function: it serves on the one hand for generating a high-frequency magnetic field and for receiving spin resonance signals, and on the other hand for generating the motion signal. However, according to the second solution the second coil system may be arranged and constructed so that it reacts substantially better to motions of the body. Moreover, continuous measurement during the entire examination is thus possible, notably also at a frequency which deviates substantially from the Larmor frequency so that the actual examination cannot be adversely affected by the formation of the motion signals.

Figure 2:
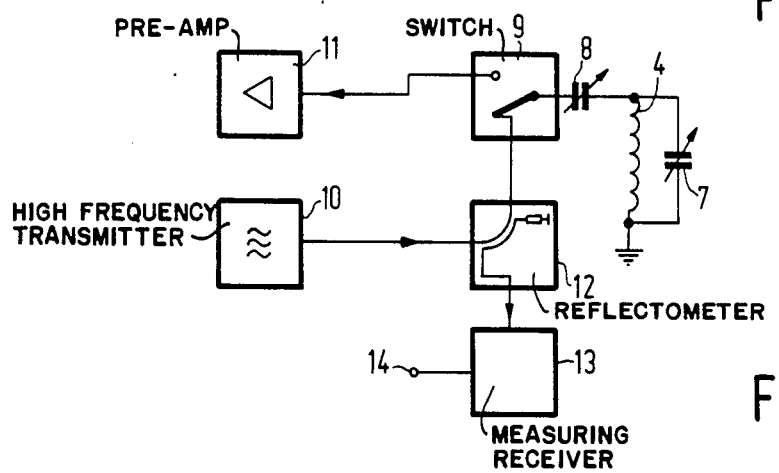
Figure 3:
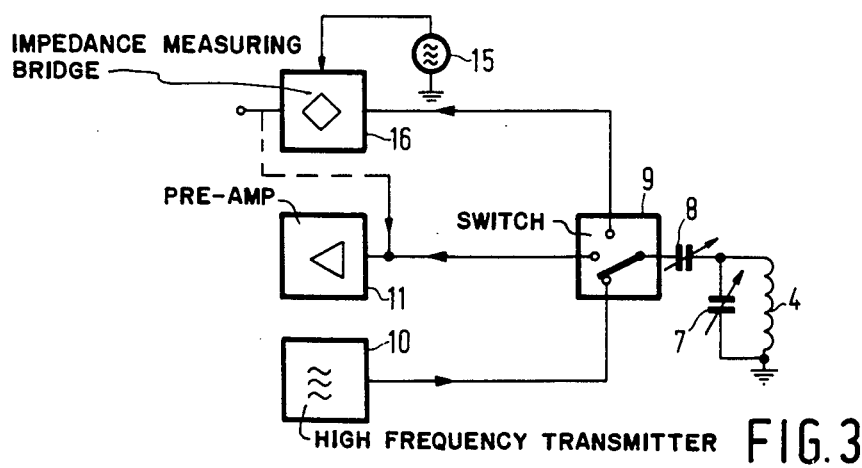
Figure 4:
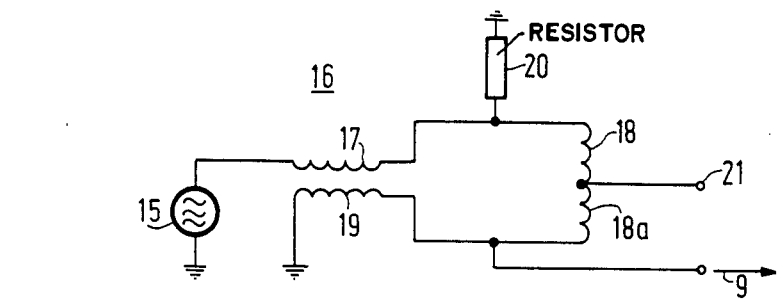
Figure 5:
Figure 6:
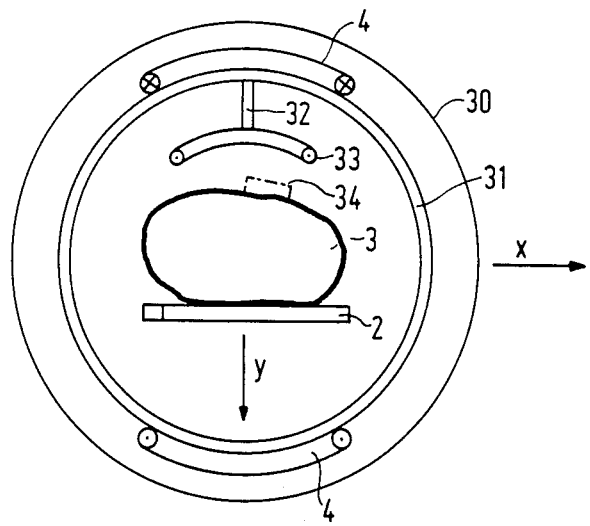
Figure 7:
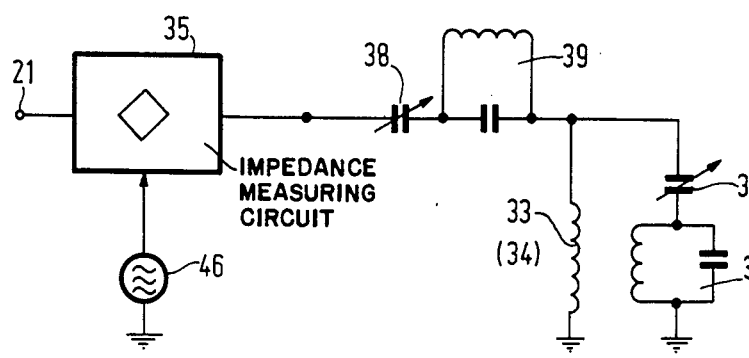

The invention will be described in detail hereinafter with reference to the attached drawings. Therein:

FIG. 1 is a diagrammatic longitudinal sectional view of a MRI tomography apparatus, FIGS. 2 and 3 show different versions of a MRI tomography apparatus in which the high-frequency coil system for exciting spin nuclei and receiving resonance signals is also used to generate the motion signal, FIG. 4 shows an impedance measurement circuit which can be used in the embodiment shown in FIG. 3, FIG. 5 shows a time diagram illustrating the operation of the high-frequency coil system, FIG. 6 is a sectional view of a MRI tomography apparatus which includes a separate high-frequency coil system for forming motion signals, and FIG. 7 shows a separate impedance measurement circuit for the MRI tomography apparatus of FIG. 6.

A MRI tomography apparatus as shown in FIG. 1 includes an electromagnet which consists of four coils 1 and which generates a strong, static, uniform magnetic field which extends in the direction of the common horizontal coil axis. A patient 3 positioned on a table 2 inside the electromagnetic is enclosed by a high-frequency coil 4 which pulse-wise generates a high-frequency magnetic field extending perpendicularly to the main magnetic field generated by the electromagnet. The frequency of the high-frequency magnetic field is proportional to the flux density of the main magnetic field which may amount to from 0.1 T to 4 T, depending on the construction of the electromagnet; and the proportionality constant corresponds to the gyromagnetic ratio (approximately 42.5 MHz/T). In the volume enclosed by the high-frequency coil 4 spin nuclei can thus be resonantly excited by the high-frequency magnetic field.

The MRI tomography apparatus also includes four gradient coils 5 generating a magnetic field which extends in the direction of the main magnetic field and which linearly varies in this direction, and also further gradient coils generating a magnetic field which also extends in the direction of the main magnetic field but which varies in two directions perpendicular thereto. When these gradient coils are energized, the phase of the signal induced in the high-frequency coil system 4 subsequent to the generating of the high frequency magnetic field is influenced in dependence of the spin nuclei distribution in the body region being examined, so that the spin nuclei distribution in a two-dimensional or three-dimensional region of the body can in principle be determined by means of such a MRI tomography apparatus.

FIG. 2 shows the block diagram of a first embodiment in accordance with the invention. The high-frequency coil system 4 thereof is supplemented with a variable capacitor 7 in order to form a parallel resonance circuit. One connection of this parallel resonance circuit is connected to ground with its other connection being connected to a switch 9 via a further variable capacitor 8. In the position of the switch 9 shown, the network 4, 7, 8 receives the electric power of a high-power high-frequency transmitter 10 whose carrier frequency corresponds to the spin resonance frequency. In the other position of the switch 9 which is not shown, the preamplifier 11 of a receiver (not shown) is connected to the network formed by the variable capacitors 7 and 8 and the high-frequency coil 4, so that it can receive the signals induced in the high-frequency coil 4 by spin resonance.

At the spin resonance frequency, the input impedance of the preamplifier 11, the output impedance of the high-frequency transmitter 10 and the impedance of the network 4, 7, 8 are equal and amount to, for example 50 ohms. This matched state is adjusted after the introduction of the patient 3 and before the beginning of the actual examination by adjustment of the capacitors 7 and 8, that is to say preferably automatically by means of an impedance measurement device (not shown). However, this matched state changes when the patient moves inside the coil, i.e. also in reaction to respiratory, deglutitory, cardiac and peristaltic motions, depending on the position of the coil, because the quality factor and the stray capacitance of the coil 4 are influenced thereby. The instantaneous value of the impedance of the network 4, 7, 8, therefore, is a measure of the actual phase of motion of the body being examined, so that motion signals can be derived therefrom.

To this end, between the power transmitter 10 and the switch 9 there is connected a reflectometer 12 whose output signal is processed in a reflection measuring receiver 13 whose output 14 supplies the motion signal. For a long as the high-frequency transmitter 10 and the network 4, 7, 8 are matched, the output signal of the reflectometer 12 will be substantially zero. In the case of mismatching, however, a part of the high-frequency power applied will be reflected; and the output of the reflectometer will then carry a high-frequency signal whose amplitude is dependent on the reflection factor or the degree of mismatching. This high-frequency signal is rectified and possibly amplified in the receiver 13, after which it appears on the output 14. This signal can subsequently be compared with presettable threshold values which correspond to given impedances and hence given phases of motion so that it can be used to initiate control procedures when it lies between the threshold values.

FIG. 5 shows a typical time chart of an examination performed by means of such a MRI tomography apparatus. During a period Ta a so-called 90° pulse is generated, i.e. the high-frequency transmitter 10 is connected to the high-frequency coil 4, by the switch 9, for such a period of time that the nuclear magnetization in the body being examined is tilted exactly 90° with respect to the direction of the main magnetic field. Subsequently, usually one or more so-called 180° pulses Tb are applied, after which the signal induced in the coil is received (interval Tc); the switch then occupies the position which is not shown in the drawing. A typical duration of this procedure is approximately 100 ms; the procedure is periodically repeated after a period of typically 600 ms which is comparatively long in comparison with the duration of the procedure itself. During each repeat the fields of the gradient coils are changed in a defined manner.

In the device shown in FIG. 2, impedance measurement is possible only during the periods during which the coil 4 receives the electric power of the high-frequency transmitter 10; in FIG. 5, therefore, these would be the periods Ta and Tb. Assuming that the body of the patient is in approximately the same phase during the comparatively closely successive periods Ta ... Tc, so-called gating will be possible by means of the motion signal derived. The spin resonance signal induced in the coil 4 during the period Tc is then evaluated when the motion signal lies within a given amplitude range, i.e. when the patient body is in a defined position. If ths is not the case, the signal induced will not be evaluated and the measurement must be repeated (using the same gradient fields).

When a triggering operation is also to be performed by means of the embodiment shown in FIG. 2, the impedance must also be measured during the comparatively long period of time elapsing between the reception of the last pulse Tc of a measurement and the transmission of the first pulse Ta of a subsequent measurement. Therefore, the high-frequency transmitter 10 must also apply a signal to the coil 4 during this period. In order to prevent these measurements from influencing the spin relaxation taking place during the period between Tc and Ta, this signal must be applied with a substantially reduced electic power and/or in defined time intervals during this period with measurement periods which are substantially shorter in comparison with the periods for Ta and Tb, if measurement does not take place at a frequency other than the Larmor frequency. The generating of the motion signals, however, is more difficult in this case because the reflected signal either has a substantially lower amplitude or must be formed during a substantially shorter period of time.

As has already been mentioned, motions of the patient influences the quality factor and the inductance of the coil, thus also causing a shift of the resonance curve of the network 7, 8, 9 to higher or lower frequencies. However, an unambiguous relationship then no longer exists between the impedance and the relevant phase of motion. This can be avoided by slightly detuning the network 4, 7, 8 with respect to the measurement frequency (usually the spin resonance frequency). Detuning should be slight with respect to the 3 dB bandwidth of the network; however, it should be so large that the resonance frequency of the network 4, 7, 8 always remains either below or above the measurement frequency in any feasible phase of motion. A suitable detuning value is 20 kHz for a 3 dB bandwidth of 300 kHz and a spin resonance frequency of approximately 85 MHz.

FIG. 3 shows a further embodiment in accordance with the invention in which corresponding parts are denoted by corresponding reference numerals. The switch 9 is connected directly to the high-frequency transmitter 10 and, contrary to the switch shown in FIG. 2, it comprises three positions. In one position, the electric power of the high-frequency transmitter 10 is applied to the network 4, 7, 8. In a second switch position, the preamplifier 11 is connected to this network and in a third switch position an impedance measuring unit is connected to the network. The impedance measuring unit consists of an additional high-frequency generator 15 and an impedance measuring bridge 16 which is powered by the high-frequency generator 15.

The impedance measuring bridge 16 may be constructed, for example as a Wheatstone bridge, and is designed so that it is balanced when the impedance of the network 4, 7, 8 corresponds to a given reference impedance, for example, 50 ohms required for matching at the frequency of the high-frequency generator 15. The power of the additional high-frequency generator 15 may be substantially lower than that of the high-frequency transmitter 10; and its frequency preferably deviates therefrom with the deviation being small in comparison with the 3 dB bandwidth of the network 4, 7, 8, but so large that the spin nuclei in the region of the body being examined are not excited thereby. Thus, the actual examination will not be influenced by the impedance measurement. It is again advantageous when the network 4, 7, 8 has a resonance frequency which deviates from the measurement frequency of the additional high-frequency generator.

Using such an arrangement, the impedance measurement can be performed each time between the periods Ta and Tb, Tb and Tc, Tc and Ta, etc. i.e. always when no magnetic field is generated by the high-frequency coil 4 or when no resonance signal is induced therein. Consequently, the motion signal generated by means of the impedance measuring unit can be used for gating as well as for triggering.

The signal on the output of the impedance measuring bridge usually requires further processing (amplification, rectifying) for which purpose an appropriate processing unit is required. However, as is denoted by a broken line in FIG. 3, it is alternatively possible to amplify the output signal of the impedance measuring bridge 16 by means of the preamplifier 11 or a part thereof. In that case there would be a dual function for the preamplifier: namely, the impedance measuring unit 15, 16 (balancing of the network 4, 7, 8 before examination, generating the motion signal during the examination) and high frequency 4 (detection of motion, excitation and reception of spin resonance signals).

FIG. 4 shows a feasible embodiment of the impedance measuring unit 15, 16 shown in FIG. 3. The high-frequency generator, one connection of which is connected to ground, then feeds an inductive RF bridge circuit which includes four inductances 17, 18, 18a and 19; the inductances 17 and 19 are equal and so are the inductances 18 and 18a. The two inductances 17 and 19 are also permanently magnetically coupled, so that a transmitter is obtained. To the junction of the inductances 17 and 18 there is connected a resistor 20, whose other connection is connected to ground and whose value corresponds to the reference impedance of the RF coil system 10 (50 ohms). The junction of the inductances 19 and 18 is connected to the network 4, 7, 8 by the switch 9 during the impedance measurement when its impedance has exactly the value (50 ohms) required for matching at the frequency of the high-frequency generator 15, and equal voltages of opposite phase appear on the connections of the inductance, so that no voltage occurs on the central tapping 21 of this inductance. In the non-matched state, the voltages on the two ends of the inductance are no longer equal so that a voltage which deviates essentially from zero appears on the central taping 21 with the voltage being a measure of mismatching.

It has been assumed thus far that the coil which generates the high-frequency magnetic field for exciting the spin nuclei also receives the spin resonance signals. However, the invention can also be used when a separate coil is used for the excitation of the magnetic field and for the reception of the spin resonance signal. The embodiment shown in FIG. 2 can then be used in conjunction with the coil required for generating the high-frequency magnetic field, while the embodiment shown in FIG. 3 can also be used in conjunction with the coil intended for the reception of the spin resonance signal.

Thus far it has been assumed that the impedance measurement takes place at a frequency which at least approximates the frequency of the spin resonance signal. However, this measurement can also take place at a second, higher resonance frequency of the network 4, 7 and 8, because the impedance thereof also varies strongly as regards magnitude and/or phase at the second resonance frequency. This offers the advantage that the impedance measurement does not influence the excitation of the spin nuclei.

For the embodiments described thus far, it has been assumed that the high-frequency coil system serves, on the one hand, for exciting the spin nuclei and for receiving the spin resonance signals, and on the other hand, for forming the motion signal. Hereinafter an embodiment will be described in which there is provided a separate high-frequency coil system for forming the motion signal.

FIG. 6 is a cross-sectional view of a part of a MRI tomography apparatus which includes such a separate high-frequency coil system. Inside a circular region 30 which corresponds to the free opening of the electromagnet 1 (FIG. 1), there is arranged the high frequency coil system 4 in which is suitable for high frequencies, as described in German Patent Application No. P 33 47 597. This two-part coil system is powered so that the current in the conductors of the upper loop which extend perpendicularly to the plane of drawing flows in the opposite direction with respect to the corresponding conductors of the lower loop. It is thus achieved that the high-frequency magnetic field generated by this coil extends perpendicularly to the static magnetic field in the x-direction.

The high-frequency coil system 4 is accommodated on a hollow cylindrical plastics body 31 which is rigidly connected to the patient table in a manner not shown. A high-frequency coil 33 which serves to generate motion signals is connected to the plastics body 31 by a support 32. The coil may also be displaceable in the y or the z direction. However, it may also be connected to the plastics body in such a manner that it is not visible for the patient; for example, it may be provided on the exterior thereof. It comprises one or more turns which are arranged so that the magnetic field generated thereby extends in the y direction. If the plastics body 31 with the high-frequency coil system 4 were situated at the area of the head of the patient, the coil 33 could also be arranged so that the field generated thereby extends in the z direction, i.e. in the longitudinal direction of the patient table or perpendicularly to the plane of the drawing in FIG. 6.

It is merely important that the magnetic field generated by the high-frequency coil 33 extends essentially perpendicularly to the magnetic field generated by the high-frequency coil system 4. This is because it is thus ensured that the high-frequency coil system 4 and the high frequency coil 33 are magnetically uncoupled from one another to a high degree; thus, on the one hand the effect of the magnetic field generated by the high-frequency coil system 4 is minimized due to the presence of the high-frequency coil 33 and on the other hand the signals induced in the high-frequency coil 33 by the high-frequency coil system 4 are also minimized.

The reference numeral 34 diagrammatically denotes a further, preferably flat coil which is positioned on the patient body 3 so that its field extends essentially also in the y direction. This coil may be constructed in the same way as the surface coils which are used only for the reception of spin resonance signals (and not for the excitation of spin nuclei) in MRI tomography. Contrary to the coil 33 which is rigidly secured to the plastics body 31, the construction of such surface coils may be adapted to the relevant application so that because of this fact and the fact that the coil can be moved very near to the region to be monitored for motions, an essentially higher sensitivity is obtained. Therefore, such coils also enable useful motion signals to be derived also from comparatively slight motions, for example, cardiac motions. On the other hand, it is necessary to attach these coils to the body of the patient before examination.

FIG. 7 shows a circuit arrangement for deriving the motion signal. The circuit arrangement includes an impedance measuring unit 35, for example, an impedance measuring bridge, a high-frequency generator 46 being connected to one branch thereof while the high-frequency coil 33 or 34 is connected to the other branch thereof via a transformation network. The frequency of the high-frequency transmitter is substantially higher than the Larmor frequency resulting from the field strength of the magnet for hydrogen. When the field strength of the magnet amounts to 2 T, for example, the Larmor frequency will be approximately 85 MHz and the frequency of the high-frequency transmitter should then be between 100 MHz and 200 MHz and should not coincide with a harmonic of the Larmor frequency. When this MRI tomography apparatus is to be also used for determining the distribution of elements other than hydrogen, for example sodium, phosphorus or fluorine the frequency must be chosen so that it does not coincide with the harmonics of the Larmor frequencies for sodium, phosphorus and fluorine which respectively amount to approximately 68 MHz, 35 MHz and 80 MHz at 2 T.

The transformation of the impedance of the high-frequency coil to a preferably real resistance of 50 ohms is performed on the one hand by means of a tuning capacitor 36 which is connected in series with a parallel resonance circuit 37, and in parallel with the high-frequency coil 33 (34) and a trimming capacitor 38, by which one end of the coil 33 (34) is connected to one branch of the impedance measuring bridge 35 in series with a parallel resonance circuit 39. The parallel resonance circuits 37 and 39 are tuned to the Larmor frequency and are designed so that their capacitive impedance at the frequency of the high-frequency transmitter 46 is lower (at least not essentially higher) than the capacitive impedance of the capacitors 36 and 38, so that the capacitive impedance in the series branch or the parallel branch can be varied by variation of the capacitance of the capacitors 36 and 38.

After introduction of the patient and possibly after fixing the high-frequency coil 34, but before the beginning of the examination, the capacitors 36 and 38 are adjusted (preferably automatically) so that the input resistance of the network formed by the high-frequency coil 33 (34) and the components 36 . . . 39 has a given value at the frequency of the high-frequency generator 46, for example, 50 ohms so that it is matched with the impedance measuring bridge. During the entire subsequent examination, the output 21 of the impedance measuring bridge 35 carries a measurement signal whose amplitude has the value zero or a minimum value in the matched condition. In reaction to motions of the patient, for example, respiratory, deglutitory, cardiac and peristaltic motions, the quality factor and the stray inductance of the coil 33 or 34 changes, thus causing a variation of the impedance of the network connected to the impedance measuring bridge 35, so that the amplitude of the output signal increases in accordance with the relevant motional phase. The signal on the output 21 can be used as the motion signal, preferably after rectification with a small time constant.

Generally, the magnetic field generated by the high-frequency coil system cannot be fully prevented from inducing a voltage in the high frequency coils 33 and 34 for generating motion signals. This is notably so when, as in the case of the high-frequency coil 34, the position thereof with respect to the high-frequency coil system is variable. Consequently, currents will flow in the circuit connected to the high-frequency coil 33 or 34, so that the high-frequency coil system 4 is loaded and the magnetic field generated thereby is distorted. Moreover, the signal on the output 21 is liable to be falsified the fact must be taken into account that the power applied to the high-frequency coil system 4 is substantially greater than the electric power applied to the high-frequency coil 33 or 34. Both effects are reduced by the resonance circuits 37 and 39 which have a high impedance at the frequency of the high-frequency coil system 4. The elements 36 . . . 39 represent a filter device which enables a withdrawal of a small amount of energy from the high frequency coil 4 by the high frequency coil 33 or 34.

The components 36 and 37 ensure that the high-frequency coil 33 or 34 operates in parallel resonance at the frequency of the high-frequency generator 46. However, when the high-frequency coil 33 (34) operates in series resonance as a result of a series connected trimming capacitor 36, the parallel connected series branch with the parallel resonance circuit 37 may be dispensed with because the series resonance circuit then formed already has a high impedance at frequencies which are remote from its series resonance frequency, such as the frequency of the high-frequency coil system 4.

An advantage of the embodiment including a separate high-frequency coil system for forming a motion signal consists in that the state of motion of the patient can be continuously determined during the entire examination or substantially the entire examination. Moreover, the magnetic field generated by the high-frequency coil 33 or 34 cannot excite spin nuclei because the frequency of the high-frequency transmitter deviates substantially from the Larmor frequency.

What is claimed is:

1. A MRI tomography apparatus for generating a motion signal comprising
   first high frequency coil means, surrounding a body to be examined, for generating a high frequency magnetic field at the Larmor frequency, said first high frequency coil means receiving spin resonance signals from said body to be examined,
   second high frequency coil means, positioned adjacent to said body and within said first high frequency coil means, for generating a motion signal, and
   impedance measuring means for measuring impedance of said second high frequency coil means to determine said motion signal.

2. A MRI tomography apparatus according to claim 1, wherein said second high frequency coil means has a resonance frequency, said resonance frequency being substantially higher than a proton resonance frequency.

3. An MRI tomography apparatus according to claim 1 or claim 2, wherein said first high frequency coil means generates a first magnetic field and said second high frequency coil means generates a second magnetic field, and wherein said second magnetic field extends substantially perpendicularly to said first magnetic field.

4. A MRI tomography apparatus according to claim 3, wherein said second high frequency coil means includes a filter device, said filter device enabling a withdrawal of a small amount of energy from said first high frequency coil means by said second high frequency coil means.

5. A MRI tomography apparatus according to claim 4, wherein said second high frequency coil means is rigidly coupled to said first high frequency coil means.

6. A MRI tomography apparatus according to claim 4, wherein said second high frequency coil means is slidable in one plane relative to said first high frequency coil means.

7. A MRI tomography apparatus according to claim 4, wherein said second high frequency coil means is positioned independently of said first high frequency coil system.

8. A MRI tomography apparatus according to claim 3, wherein said impedance measuring means measures said impedance of said second high frequency coil means at a frequency deviating slightly from a resonance frequency of said second high frequency coil means.

9. A MRI tomography apparatus according to claim 1 or claim 2, wherein said second high frequency coil means includes a filter device, said filter device enabling a withdrawal of a small amount of energy from said first high frequency coil means by said second high frequency coil means.

10. A MRI tomography apparatus according to claim 1 or claim 2, wherein said second high frequency coil means is rigidly coupled to said first high frequency coil means.

11. A MRI tomography apparatus according to claim 1 or claim 2, wherein said second high frequency coil means is slidable in one plane relative to said first high frequency coil means.

12. A MRI tomography apparatus according to claim 1 or claim 2, wherein said second high frequency coil means is positioned independently of said first high frequency coil system.

13. A MRI tomography apparatus according to claim 1 or claim 2, wherein said impedance measuring means measures impedance at a frequency different from a spin resonance frequency measured by said first high frequency coil means.

14. A MRI tomography apparatus according to claim 1, wherein said impedance measuring means measures said impedance of said second high frequency coil means at a frequency deviating slightly from a resonance frequency of said second high frequency coil means.

* * * * *

UNITED STATES PATENT AND TRADEMARK OFFICE
CERTIFICATE OF CORRECTION

PATENT NO. : 4.694.836
DATED : September 22, 1987
INVENTOR(S) : Dirk Buikman, et al.

It is certified that error appears in the above-identified patent and that said Letters Patent is hereby corrected as shown below:

IN THE TITLE PAGE

Inventors    change "Peter Röschman" to
--Peter Röschmann--

Signed and Sealed this

Thirteenth Day of September, 1988

Attest:

DONALD J. QUIGG

Attesting Officer    Commissioner of Patents and Trademarks